(12) United States Patent
Jörneus et al.

(10) Patent No.: US 6,276,938 B1
(45) Date of Patent: Aug. 21, 2001

(54) METHOD AND ARRANGEMENT FOR EXECUTING A CEMENTED SUPERSTRUCTURE AND ALSO DISTANCE MEMBER AND SET OF DISTANCE MEMBERS

(75) Inventors: Lars Jörneus, Frillesås (SE); Bjarne Kvarnström, Huntington Beach, CA (US)

(73) Assignee: Nobel Biocare AB (SE)

( * ) Notice: Subject to any disclaimer, the term of this patent is extended or adjusted under 35 U.S.C. 154(b) by 0 days.

(21) Appl. No.: 09/424,358

(22) PCT Filed: May 27, 1998

(86) PCT No.: PCT/SE98/00994

§ 371 Date: Feb. 22, 2000

§ 102(e) Date: Feb. 22, 2000

(87) PCT Pub. No.: WO98/55040

PCT Pub. Date: Dec. 10, 1998

(30) Foreign Application Priority Data

Jun. 3, 1997 (SE) .................................................. 9702144

(51) Int. Cl.[7] .................................................. A61C 13/12
(52) U.S. Cl. ....................................... 433/172; 433/201.1
(58) Field of Search .................................. 433/172, 173, 433/174, 175, 176, 201.1

(56) References Cited

U.S. PATENT DOCUMENTS

| | | | |
|---|---|---|---|
| 5,052,929 | * 10/1991 | Seal | 433/173 |
| 5,064,375 | 11/1991 | Jörnéus . | |
| 5,108,288 | * 4/1992 | Perry | 433/173 |
| 5,145,371 | 9/1992 | Jörnéus . | |
| 5,302,125 | * 4/1994 | Kownacki et al. | 433/172 |
| 5,564,921 | * 10/1996 | Marlin | 433/172 |
| 5,674,069 | * 10/1997 | Osorio | 433/172 |
| 5,733,122 | * 3/1998 | Gordon | 433/172 |
| 5,873,720 | 2/1999 | Jorneus et al. . | |

* cited by examiner

Primary Examiner—Todd E. Manahan
(74) Attorney, Agent, or Firm—Connolly Bove Lodge & Hutz LLP

(57) ABSTRACT

A distance member is designed so as to make possible a cemented superstructure in the jaw and can be fastened to the implant in the jaw by means of a screw member. The distance member has a prefabricated external shape which is individually adapted to the respective dental situation in question for the purpose of rendering unnecessary substantial shape modification work in connection with construction of the superstructure in the jaw. The prefabricated shape has a shelf-shaped projecting part located between the upper and lower parts of the distance member and the distance member is designed with an internal counterholder which prevents torque being transmitted from the tool to the implant.

28 Claims, 6 Drawing Sheets

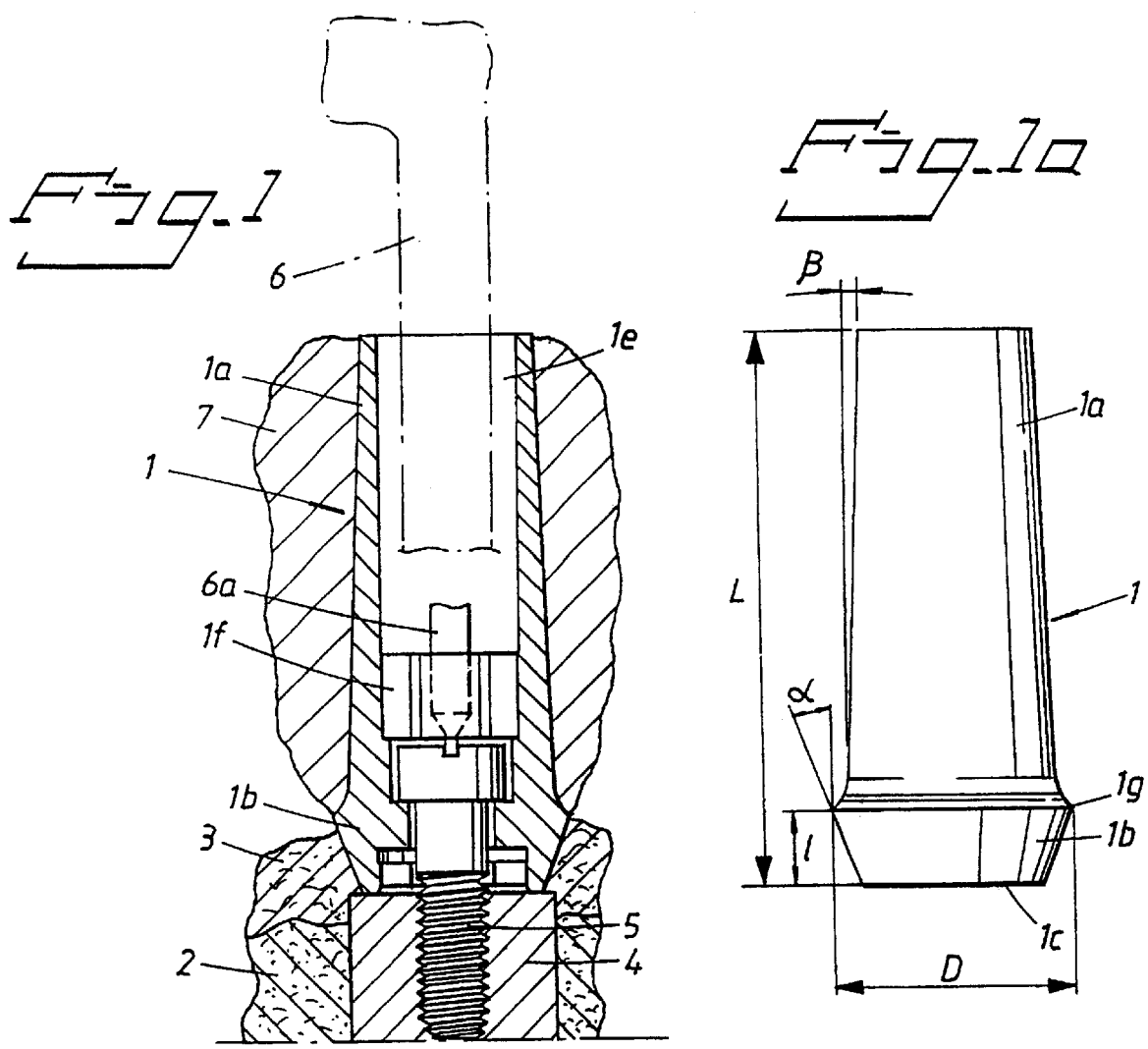

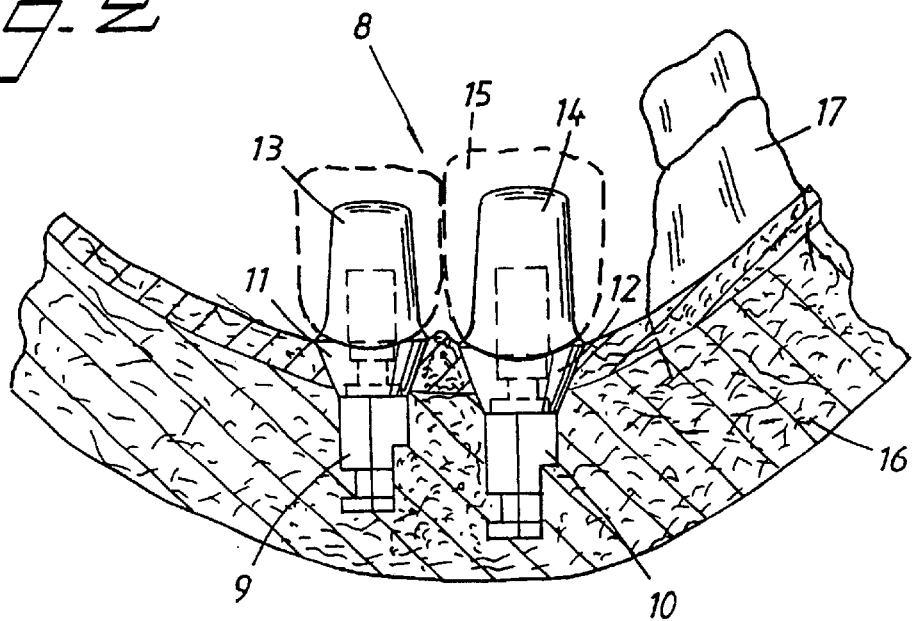
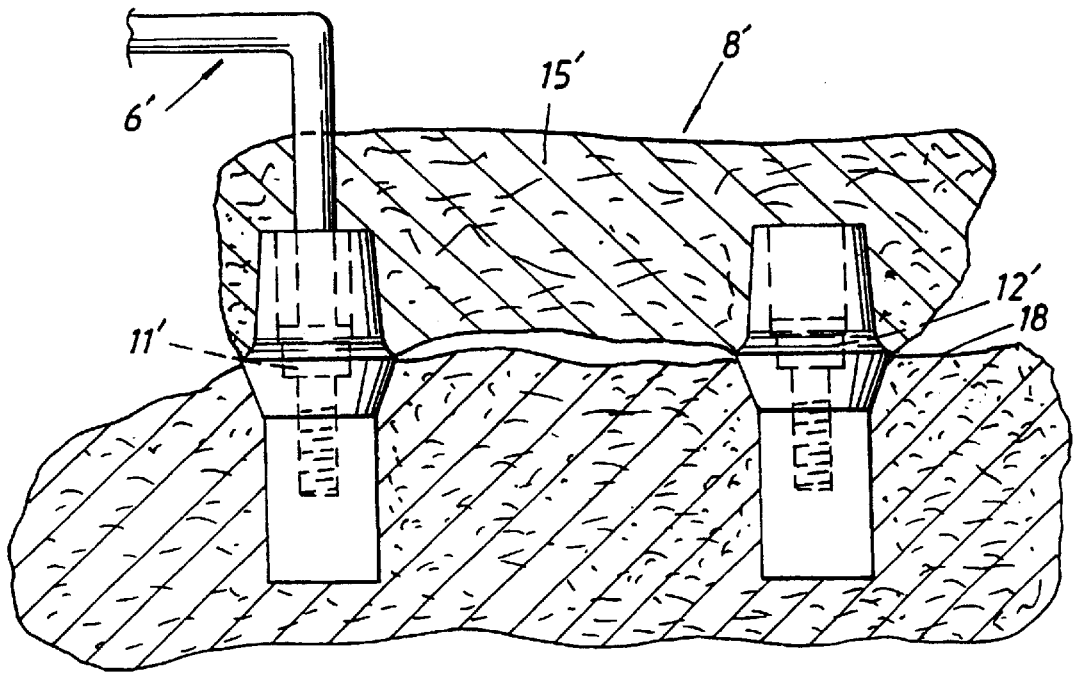

METHOD AND ARRANGEMENT FOR EXECUTING A CEMENTED SUPERSTRUCTURE AND ALSO DISTANCE MEMBER AND SET OF DISTANCE MEMBERS

TECHNICAL FIELD

The present invention relates inter alia to a method for executing a cemented superstructure on one or more distance member(s) which can respectively be mounted on an implant assigned to it (them) in the jaw (human jaw) by means of a screw member. The invention also relates to an arrangement for such a cemented superstructure in the jaw, where one or more distance member(s) can be mounted on implants assigned to it (them) with the aid of screw members. In the finished state, the superstructure has no access passage for the respective screw member(s). The invention also relates to a set of distance members which can respectively be mounted on an implant assigned to them in the jaw by means of a screw member, where one or more distance member(s) is (are) intended to form part, in the jaw, of a cemented superstructure which, in the finished state, has no access passage for the respective screw member(s). The invention also relates to a distance member for making possible a cemented superstructure in the jaw, which member can be fastened to the implant in the jaw by means of a screw member.

STATE OF THE ART

It is previously known to form a cemented superstructure on distance members anchored in implants in the human jaw. It is also previously known to design distance members with counterholders in order to prevent the transmission of torsional or torque forces to the implant in connection with tightening by means of tools. As an example of other counterholding functions in connection with such tools, refer inter alia to Swedish patent 466 786. It is also previously known to individually adapt distance members to different dental situations. In different dental situations, it is also previously known to make use of screw member sets, from which the selection for the situation concerned can be made.

DESCRIPTION OF THE INVENTION

TECHNICAL PROBLEM

In a cemented superstructure, problems arise inter alia because there are no access holes for the respective screw member(s) in the finished structure. During adjustment and repair work in such structures, difficulties thus occur with regard to freeing these structures from the implants without the risk arising of the structure and/or the implants being destroyed. Measures aimed at reducing to the greatest possible extent the requirement for carrying out repair work on finished superstructures involve placing special demands on the screw joints so that these do not loosen on the dental bridge or dental crown once it has been completed. It is also important that the components forming part of the dental bridge or equivalent can be designed and constructed so that the technical dental work is facilitated to the greatest possible extent. Major grinding-down and shape modification work during production of the superstructure and cementing are preferably to be avoided, not least out of consideration for the patient. This also applies to impression-taking and model-production work.

The invention aims to solve inter alia these problems. By means of the invention, it is possible, for example, to obtain a visual indication of the delimiting line of the dental bridge or dental crown in relation to the respective distance piece. By means of the invention, great adaptability to different individual appearances and positions in the jaw is also made possible, which is a necessary prerequisite because of the great individual differences represented by patients. It is also important that the distance member set can provide for shapes that can be related to existing incorporation-type distance pieces. It is thus important, for example, that the distance members have cone angles that essentially correspond to those of incorporation-type distance pieces so that bone and soft tissue do not get in the way when the distance members are mounted. The invention also solves these problems.

SOLUTION

The new method according to the above can mainly be considered to be characterized in that a set of distance members which are intended for different individual dental situations is provided, in that each respective distance member in the set provided is made with an internal counterholder for a tightening tool that is used when tightening the respective screw member, which counterholder prevents torque being transmitted from the tightening tool to the implant during tightening, in that a considerable number, preferably at least 80%, of the distance members in the set are individually externally shaped so as to provide for individual anatomical shapes which are impressed on the cementing function and which are optimized for a number of main types of dental situations, by means of which impression substantial modification work on the respective anatomical shape in connection with construction of the cemented superstructure in the jaw is essentially rendered unnecessary, and in that one or more distance member(s) that is (are) optimum or most practicable for the given dental situation is (are) selected from the set of distance members provided.

An arrangement according to the type indicated in the introduction is characterized by the following combination, that is to say in that each respective distance member is made or provided with an internal counterholder member for a tightening tool, which counterholder member is designed to prevent torque being transmitted from the tool to the respective implant in connection with tightening of the respective screw member, in that each respective distance member has a prefabricated external shape which is essentially individualized to the given dental situation, and in that the prefabricated individual external shape of the respective distance member is likewise designed to comply with the cementing function requirements involved without the need for substantial shape modification work during construction of the superstructure.

The new set of distance members can mainly be considered to be characterized by the following combination, that is to say in that the distance members are designed with prefabricated individual external shapes which are adapted to main types of different dental situations, in that the prefabricated individual external shape of a considerable proportion, at least 80%, of the set is designed to comply with the cementing function involved without the need for substantial shape modification work during construction of the superstructure in the jaw, and in that each respective distance member is made or provided with an internal counterholder member for a tightening tool, which counterholder member is designed to prevent torque being transmitted from the tool to the implant concerned in connection with tightening of the respective screw member.

Embodiments of the set of distance members emerge from the subclaims below.

A distance member according to the invention can mainly be considered to be characterized by the following combination which is characterized in that the distance member is assigned a prefabricated external shape, in that the prefabricated external shape is individually adapted to a given dental situation for the purpose of rendering unnecessary substantial shape modification work in connection with construction of the superstructure in the jaw, in that the prefabricated shape has a shelf-shaped projecting part or projecting flange located between the upper and lower parts of the distance member, and in that the distance member is or can be designed with an internal counterholder which prevents torque being transmitted from the tool to the implant.

Embodiments of the distance member according to the invention emerge from the subclaims below.

ADVANTAGES

By means of the above proposals, it is possible to propose a distance member set which complies with a very large number of main types of dental situations, which in turn means that considerable optimization is possible for the majority of dental situations. Use can be made of existing principles with regard to tightening tools with counterholders. Visual indications of the connection of the replacement material to the distance member and implant can be obtained. Grinding and adaptation work can be considerably reduced, as can patient treatment time. The invention can be made applicable for distance members made of various materials (titanium, gold, ceramics etc.).

DESCRIPTION OF THE FIGURES

A currently proposed embodiment of the method, the arrangement, the set of distance members and the distance member is to be described below with simultaneous reference to the attached drawings, in which FIGS. 1–1c show in longitudinal section and side and end views a first exemplary embodiment of a distance member, where the tightening tool has also been indicated symbolically, FIG. 2 shows in perspective parts of a lower jaw, into which implants have been surgically inserted, distance members, which have been provided with a superstructure in the form of a dental bridge, being fastened to the implants, FIG. 3 shows in vertical section parts of a human lower jaw and, arranged therein, implants on which a superstructure has been mounted.

DETAILED EMBODIMENT

Figure 4:
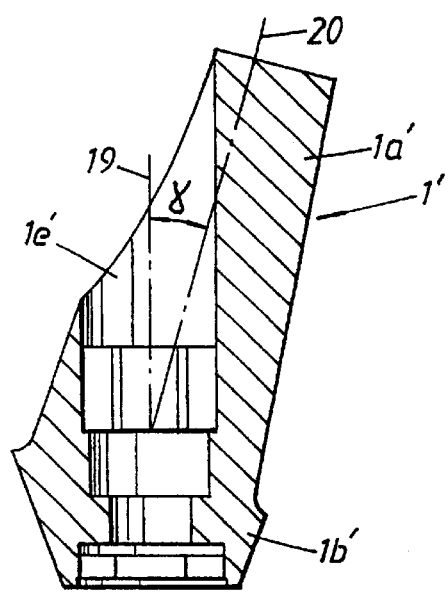
FIGS. 4–17 show in cross-section and side views a number of distance members of various constructions, which form part of a set.

FIGS. 1–1c show a first embodiment of a distance member 1. In FIG. 1, dentine is represented symbolically by 2 and soft tissue of the dentine by 3. An implant which has been incorporated into the dentine is designated by 4. The distance member is screwed into the implant by a screw 5 which has an external thread which interacts in a known manner with an internal thread in the implant. The distance member has an upper part 1a and a lower part 1b. A lower surface 1c (FIG. 1a) bears against an upper surface on the implant, likewise in a known manner. The distance member is coned upwardly/outwardly from the lower surface 1c and the half angle α of the cone is roughly 20°. The length L of the distance member is roughly 11 mm and the length 1 of the lower part 1b is roughly 1.5 mm. The lower part 1b is provided with an internal hexagonal recess (FIG. 1b), by means of which the distance member is rotationally fixed relative to the implant which has a hexagonal nut projecting up into the hexagonal recess. The distance member has an internal recess 1e, in the bottom part of which a counterholder member if is arranged. Via the recess and the counterholder member, a tightening tool 6 for the screw 5 is introduced. The tool may be of a type known per se and include a screwdriver 6a which can be brought into engagement with a screwdriver recess in the screw in a known manner. By means of the counterholder member, torsional forces are prevented from being transmitted from the tool to the body of the distance member and in this way torsional forces are prevented from being transmitted from the tool to the implant 4. The counterholder member is arranged in a rotationally fixed manner in the recess 1e, cf. FIG. 1c.

It is also characteristic of the distance member 1 that it has a transition 1g which is made in the form of an upwardly directed (in FIG. 1a) shelf which marks the transition between the upper and lower parts 1a and 1b respectively of the distance piece. According to the exemplary embodiment, the upper part is to be covered by a dental bridge or crown, the material of which is indicated by 7 in FIG. 1. The edge of the transition forms a visually noticeable edge which facilitates the work of the dentist and the modelmaker. The diameter D of the transition is roughly 4.5 mm in the case shown. The transition 1g is also characterized by a sharp external corner which becomes a concave upwardly directed radius R of roughly 1 mm. The upper part is coned upwardly/inwardly and its half cone angle β is roughly 2°.

FIG. 2 indicates by 8 a superstructure in the form of a dental bridge on and between two implants 9 and 10. A distance member 11 and 12 respectively according to the above is fastened on each respective implant. The superstructure includes sleeves 13 and 14 respectively and bridge material 15. The jaw is symbolized by 16 and teeth therein by 17.

FIG. 3 shows on enlarged scale the superstructure 8' and the bridge material 15'. The visible line or transition is designated here by 18. Screw tightening by means of the tool 6' is effected in a stage before the application of the cement 15'. The cementing is effected in such a manner that, in the finished state, there are no access holes for the screw members 11' and 12' respectively.

FIG. 4 shows in longitudinal section a further embodiment of a distance member. In this case, the upper and lower parts 1a' and 1b' are angled in relation to one another. This means that the length of the lower part (cf. 1 in FIG. 1a) varies around the periphery. In the figure, the centre line of the lower part is indicated by 19 and the centre line of the upper part is indicated by 20. According to the embodiment shown, said centre line is inclined at an angle χ of roughly 20°. The recess 1e' has as its centre line the centre line 19 of the lower part and in this way the recess extends obliquely in the inclined upper part 1a'.

Figure 5:
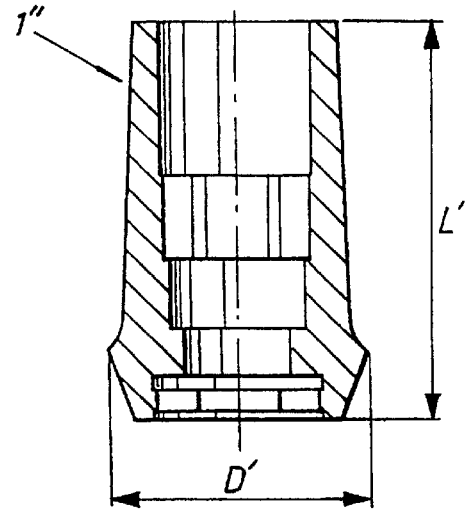

FIG. 5 shows a further embodiment where the length L' and the diameter D' differ from the corresponding length and diameter in the embodiment described above.

Figure 6:
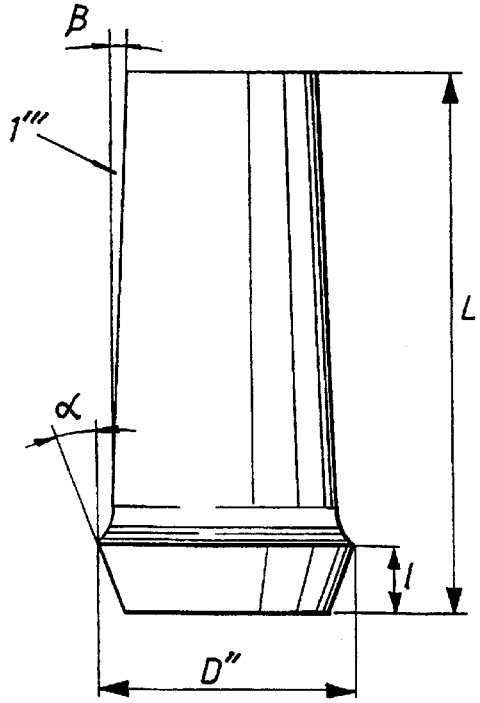

The embodiment according to FIG. 6 has the same length L as the embodiment according to FIG. 1a while, on the other hand, the diameter D" differs from the diameters D and D' respectively according to the above.

Figure 7:
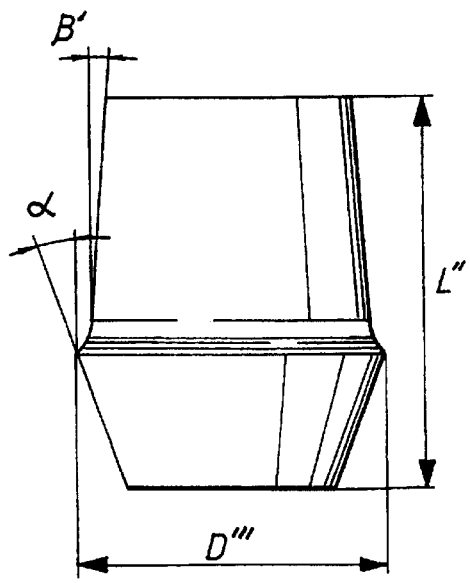

FIG. 7 shows an embodiment with different values for the length L''' and the diameter D''' and also the half cone angle β'. These values may be selected to be roughly 8 mm, roughly 6 mm and roughly 4° respectively.

Figure 8:
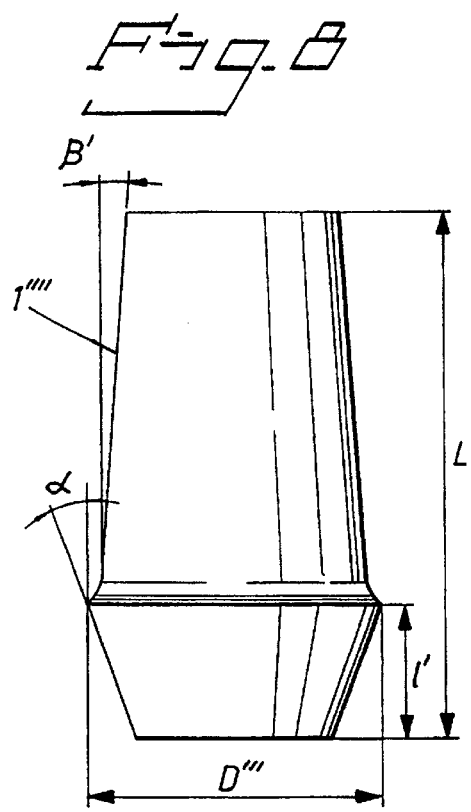

In the embodiment according to FIG. 8, the length 1' has been increased in relation to the embodiments according to the above. In this case, the diameter D'" and the angle β' apply, cf. above.

Figure 9:
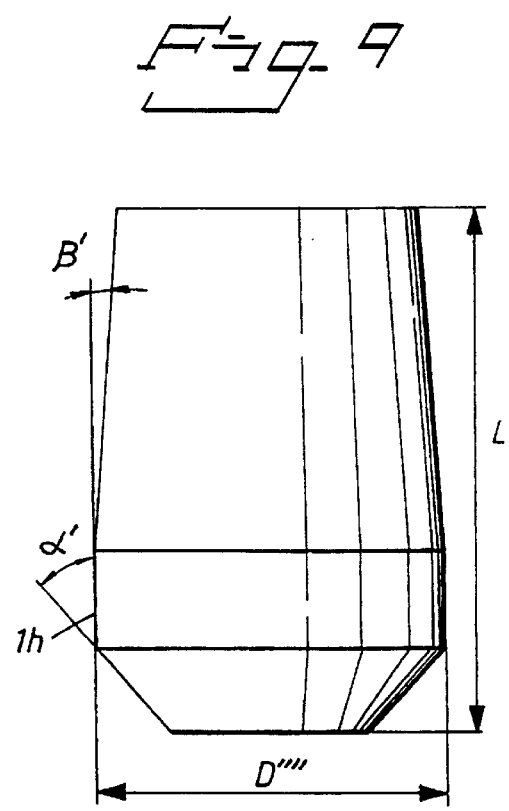

In the embodiment according to FIG. 9, the distance member has a transition part 1$h$ which is essentially cylindrical and is roughly 2 mm long. The angle α' has in this case been selected to be roughly 40°. The diameter D"" has been selected to be roughly 7 mm. The length L and the angle β' apply in this case.

Figure 10:
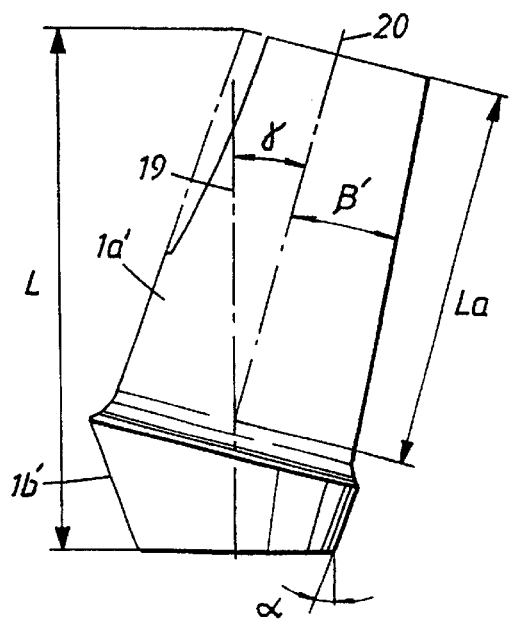

The embodiment according to FIG. 10 shows a variant where the upper and lower parts 1$a'$ and 1$b'$ respectively have been angled in relation to one another in accordance with the embodiment according to FIG. 4. The angle $\chi$ between the centre lines 19 and 20 is selected to be roughly 15° and β' is selected to be roughly 4°. The angle α 20° is also used in this case. In this case, a length La, representing the length of the upper part, has been selected to be roughly 8 mm.

Figure 11:
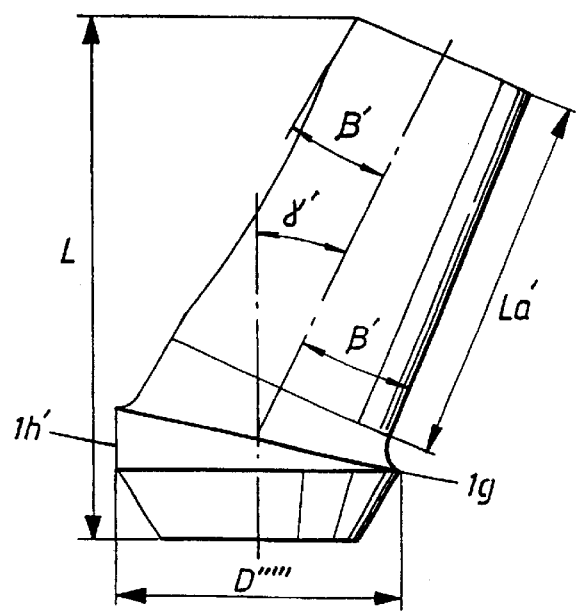

The embodiment according to FIG. 11 differs from the embodiment according to FIG. 9 in that the values of the angle $\chi'$ and the length La' have been changed to roughly 25° and roughly 7.75 mm respectively. Moreover, the transition between the upper and lower parts is asymmetrical around the periphery with a greatest straight part 1$h'$ on the far left in the figure and a sharp transition 1$g$ on the far right in the figure. Moreover, a value of roughly 5.8 mm is used for the diameter D''''.

Figure 12:
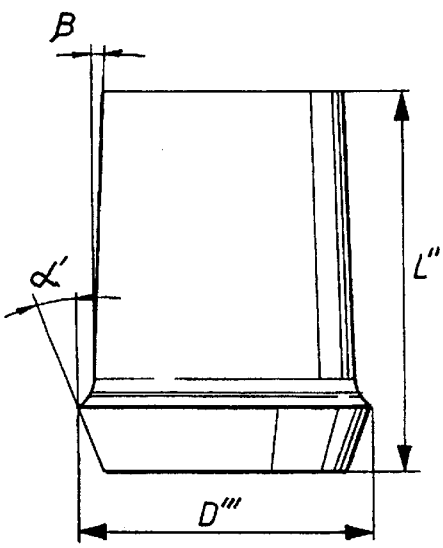

The embodiment according to FIG. 12 shows a new combination of the values for the length L", the angle α', the angle β and the diameter D'".

Figure 13:
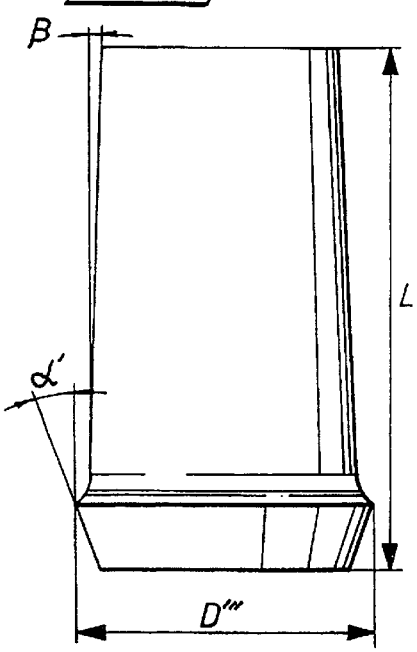

FIG. 13 shows a further combination of length, angles and diameter.

Figure 14:
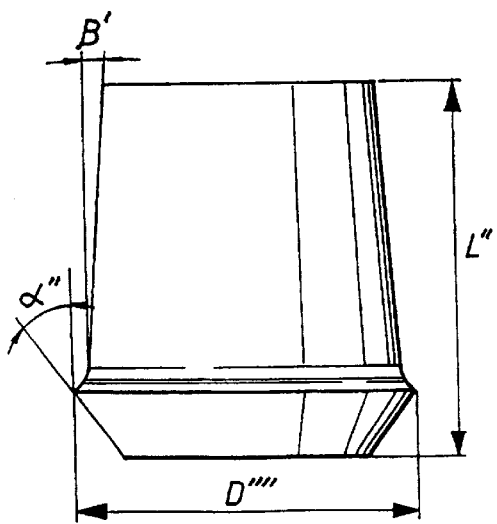

In FIG. 14, the size of the angle α is roughly 35°. Otherwise, the values L", diameter D"" and angle β' are used, cf. above.

Figure 15:
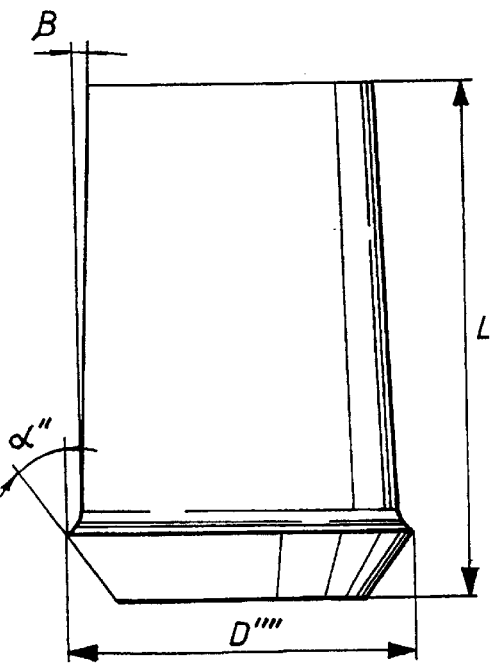

The embodiment according to FIG. 15 uses the values L, angle α', angle β and diameter D"", cf. above.

Figure 16:
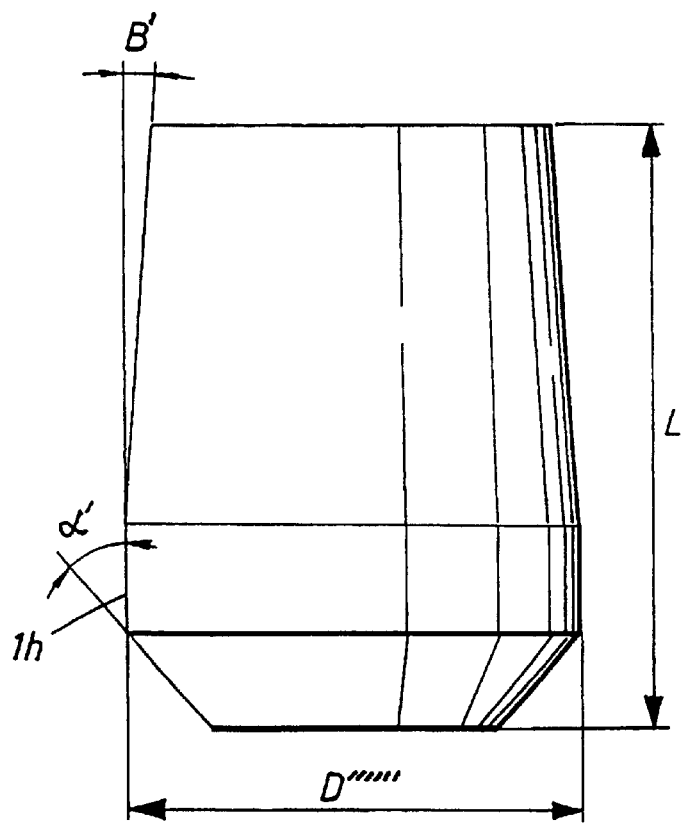

In the embodiment according to FIG. 16, a diameter D''''' of roughly 8 mm is used. Moreover, the values for the length L, the angle α', the angle β' and the transition 1$h$ are used, cf. above.

Figure 17:
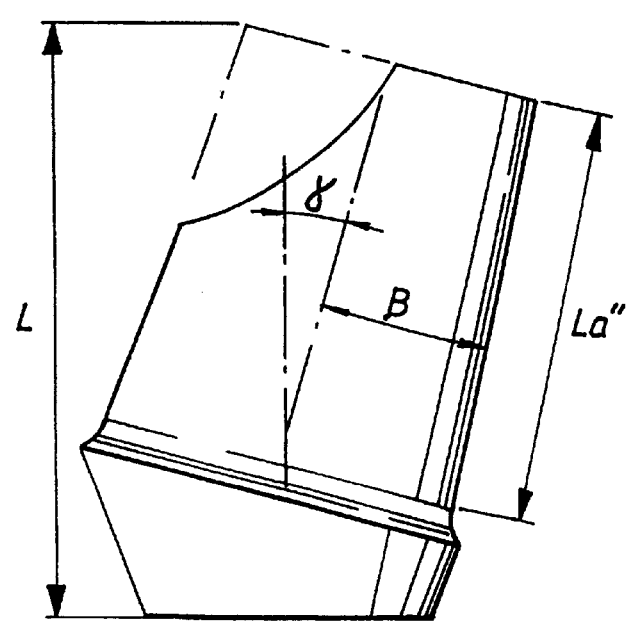

The embodiment according to FIG. 17 shows a new angled variant where the value of the length La" is roughly 7.7 mm. Moreover, the values L, β and $\chi$ as above are used for the length concerned and the angles respectively.

According to the above, angles, lengths and diameters with the same reference designations have the same values, e.g. the designation L has the single length value of roughly 11 mm, the length L" has the single value of roughly 8 mm etc. The various distance pieces have in principle the reference designations 1, 1', 1", 1''', 1"" etc.

The invention is not limited to the embodiment shown above by way of example but can be subjected to modifications within the scope of the patent claims below and the inventive idea.

What is claimed is:

1. A method of executing a cemented superstructure wherein an implant is secured to a human jaw by means of a screw member threadably engaged with the implant, mounting a distance member over the implant, and passing the screw member through the distance member and into the implant, characterized in providing a set of distance members which are intended for different individual dental situations, providing each distance member with an internal counterholder, providing a majority of the distance members in the set with individually external different shapes so as to provide for individual anatomical shapes which are impressed on the cementing function and which are optimized for a number of main types of dental situations to minimize substantial modification work on the respective anatomical shapes in connection with the construction of the cemented superstructure in the jaw, selecting at least one distance member from the set for the mounting on the implant, mounting the distance member over the implant, inserting a tightening tool into the distance member, engaging the tightening tool with the counterholder and with the screw member, preventing torque from being transmitted from the tightening tool to the implant during the tightening of the screw member as a result of the engagement of the counterholder with the tightening tool, removing the tightening tool after the implant has been tightened, and applying a cemented superstructure around the distance member.

2. The method according to claim 1, characterized in applying the superstructure in such a manner that there is no access passage for the respective screw member.

3. The method according to claim 1, characterized in that at least 80% of the distance members in the set are provided which differ individual externally from each other.

4. The method according to claim 1, characterized in that each of the distance members has an upper part and a lower part, and each lower part being conically shaped upwardly and inwardly.

5. An arrangement for a cemented superstructure in the human jaw comprising the combination of an implant and a distance member mounted on the implant and a screw extending through a longitudinal bore in the distance member and threadably engaged with the implant, characterized in that the distance member is one of a plurality of a set of distance members, each of the distance members being of one piece construction having an internal counterholder in its longitudinal bore for engagement with a tightening tool to prevent torque being transmitted from the tool to the implant during the tightening of the screw member, each the distance members having a prefabricated external shape to provide essentially individualized shapes for given dental situations with the prefabricated individual external shape of a respective distance member being designed to comply with the cementing function requirements involved to minimize the need for substantial shape modification work during construction of the superstructure, each of the distance members having an upper part and a lower part, and the upper part being conically shaped upwardly and inwardly.

6. The arrangement according to claim 5, characterized in that the upper part and the lower part of the distance member are connected to each other by a shelf-shaped projecting part.

7. The arrangement according to claim 6, characterized in that the projecting part terminates in a sharp external edge which then is curved upwardly with a concave radius.

8. The arrangement according to claim 6, characterized in that the projecting part comprises a transition capable of being an indicating surface to indicate the relation between the location of the implant and the location of a dental material that would cover the distance member.

9. The arrangement according to claim 5, characterized in that the lower part diverges conically upwardly and outwardly, a majority of the distance members in the set differing from each other with regard to at least one of the parameters of the lengths and the diameters at a transition of the upper part to the lower part and with regard to the conical angle of the lower part and the conical angle of the upper part and with regard to angle of inclination of the center line of the upper part with respect to the center part of the lower part.

10. The arrangement according to claim 5, characterized in that at least 80% of the distance members differ externally from each other.

11. The arrangement according to claim 5, characterized in that the lower part is conically shaped upwardly and outwardly at a half cone angle between 20° and 40°.

12. The arrangement according to claim 5, characterized in that the distance member lower part has a length of 1–3mm.

13. The arrangement according to claim 12, characterized in that the length of the lower part is about 1.5mm.

14. A set of distance members which can respectively be mounted on an implant in the human jaw by means of a screw member extending through a distance member and into the implant, characterized in that each of the distance members has a longitudinal bore, each of the distance members being of one piece construction having an internal counterholder in the longitudinal bore for engagement with a tightening tool to prevent torque being transmitted from the tool to the implant during the tightening of the screw member, each of the distance members having a prefabricated external shape to provide essentially individualized shapes for given dental situations with the prefabricated individual external shape of a respective distance member being designed to comply with the cementing function requirements involved to minimize the need for substantial shape modification work during construction of the superstructure, each of the distance members having an upper part and a lower part, and the upper part being conically shaped upwardly and inwardly.

15. The set according to claim 14, characterized in that the upper part and the lower part of the distance member are connected to each other by a shelf-shaped projecting part.

16. The set according to claim 15, characterized in that the projecting part comprises a transition capable of being an indicating surface to indicate the relation between the location of the implant and the location of a dental material that would cover the distance member.

17. The set according to claim 15, characterized in that the projecting part terminates in a sharp external edge which then is curved upwardly with a concave radius.

18. The set according to claim 14, characterized in that the lower part diverges conically upwardly and outwardly, a majority of the distance members in the set differing from each other with regard to at least one of the parameters of the lengths and the diameters at a transition of the upper part to the lower part and with regard to the conical angle of the lower part and the conical angle of the upper part and with regard to angle of inclination of the center line of the upper part with respect to the center part of the lower part.

19. The set according to claim 18, characterized in that at least 80% of the distance members differ externally from each other.

20. The set according to claim 14, characterized in that the lower part is conically shaped upwardly and outwardly at a half cone angle between 20° and 40°.

21. The arrangement according to claim 14 characterized in that the distance member lower part has a length of 1–3mm.

22. A distance member for making possible a cemented superstructure in the jaw which member can be fastened to an implant in the jaw by means of a screw member, characterized in that the distance member is of one piece construction and includes an upper part and a lower part, a longitudinal bore extending completely through the distance member, an exposed recess at the end of the bore in the lower part for engagement with an implant, the distance member having a prefabricated external shape to be individually adapted to a given dental situation for the purpose of rendering unnecessary substantial shape modification work in connection with construction of the superstructure in the jaw, the prefabricated shape having a shelf shaped projecting flange at the transition of the upper part and the lower part, an internal counterholder in the longitudinal bore to prevent torque being transmitted from a tool to the implant, and the upper part being conically shaped upwardly and inwardly.

23. The distance member according to claim 22, characterized in that the transition is designed with a sharp external upper surface which curves upwardly with a concave radius.

24. The distance member according to claim 22, characterized in that the lower part is conically shaped upwardly and outwardly at a half cone angle between 20° and 40'.

25. The distance member according to claim 22, characterized in that the projecting part comprises a transition capable of being an indicating surface to indicate the relation between the location of the implant and the location of a dental material that would cover the distance member.

26. The distance member according to claim 22, characterized in that the lower part is conically shaped upwardly and outwardly at a half cone angle between 20° and 40°.

27. The distance member according to claim 22, characterized in that the distance member lower part has a length of 1–3mm.

28. The distance member according to claim 22, characterized in that the distance member is made from a material selected from the group consisting of titanium, gold and ceramic.

\* \* \* \* \*